United States Patent
White et al.

[19]

[11] Patent Number: 5,902,340
[45] Date of Patent: May 11, 1999

[54] METHOD OF ASSEMBLING A MODULAR PROSTHESIS USED FOR BONE REPLACEMENT

[75] Inventors: Patrick M. White, Sacramento; Daniel E. E. Hayes, Jr., Placerville; Robert-Jan Enzerink, Davis, all of Calif.

[73] Assignee: Hayes Medical, Inc., Sacramento, Calif.

[21] Appl. No.: 08/950,034

[22] Filed: Oct. 14, 1997

Related U.S. Application Data

[62] Division of application No. 08/739,389, Oct. 29, 1996, Pat. No. 5,725,592.

[51] Int. Cl.⁶ .................................................. A61F 2/32
[52] U.S. Cl. ............................. 623/22; 623/16; 623/18; 623/19
[58] Field of Search ...................... 606/72, 60, 65–69, 606/86, 87, 89, 90, 92, 99, 100, 102; 623/18, 22, 23, 16

[56] References Cited

U.S. PATENT DOCUMENTS

| | | | |
|---|---|---|---|
| 4,790,854 | 12/1988 | Harder et al. | 623/20 |
| 4,908,032 | 3/1990 | Keller | 623/23 |
| 4,938,773 | 7/1990 | Strand | 623/23 |
| 5,002,578 | 3/1991 | Luman | 623/23 |
| 5,026,399 | 6/1991 | Engelbrecht et al. | 623/18 |
| 5,133,760 | 7/1992 | Petersen et al. | 623/20 |
| 5,133,771 | 7/1992 | Duncan et al. | 623/23 |
| 5,194,066 | 3/1993 | Van Zile | 623/20 |
| 5,314,479 | 5/1994 | Rockwood, Jr. et al. | 623/19 |
| 5,342,366 | 8/1994 | Whiteside et al. | 606/102 |
| 5,344,457 | 9/1994 | Pilliar et al. | 623/16 |
| 5,443,523 | 8/1995 | Mikhail | 623/23 |
| 5,489,309 | 2/1996 | Lackey et al. | 623/19 |
| 5,489,311 | 2/1996 | Cipolletti | 623/20 |
| 5,507,817 | 4/1996 | Craig et al. | 623/18 |
| 5,620,445 | 4/1997 | Brosnahan et al. | 606/63 |
| 5,653,765 | 8/1997 | McTighe et al. | 623/23 |
| 5,658,338 | 8/1997 | Tullos et al. | 623/18 |
| 5,665,121 | 9/1997 | Gie et al. | 623/16 |
| 5,766,263 | 6/1998 | Grundei et al. | 623/23 |
| 5,827,285 | 10/1998 | Bramlet | 606/60 |

FOREIGN PATENT DOCUMENTS

| | | | |
|---|---|---|---|
| 0 243 298 A2 | 10/1987 | European Pat. Off. | A61F 2/36 |
| 0 611 225-A1 | 8/1994 | European Pat. Off. | A61F 2/36 |
| 43 20 086 A1 | 12/1994 | Germany | A61F 2/36 |

*Primary Examiner*—Michael J. Milano
*Assistant Examiner*—Tram A. Nguyen
*Attorney, Agent, or Firm*—Wilson, Sonsini, Goodrich & Rosati

[57] ABSTRACT

The invention provides a modular three-component assembly for replacing a portion of a patient's femur or humerus. A neck component attaches directly to a stem component that inserts into the bone, and a body component that also inserts into the bone is attached to the neck component and/or to the stem component. Methods for assembling the prosthesis are also provided, wherein the stem component is inserted within the body component, and the stem component is joined to the neck component. The prosthesis may be constructed from the components outside of the patient, or, components of the prosthesis may be inserted into the patient prior to final assembly of the prosthesis during surgery.

27 Claims, 5 Drawing Sheets

METHOD OF ASSEMBLING A MODULAR PROSTHESIS USED FOR BONE REPLACEMENT

This application is a divisional of application Ser. No. 08/739,389, filed Oct. 29, 1996, now U.S. Pat. No. 5,725,592.

BACKGROUND

Replacing portions of a deteriorated or broken hip or shoulder has become an increasingly frequent operation that surgeons perform. One prosthesis that is commonly used replaces either a portion of the femur that connects with the pelvis or a portion of the humerus that attaches into the glenoid cavity of the shoulder. A variety of these prostheses have been developed, and they can be classified into one of three classifications that are based on the number of components that fit together to form the prosthesis.

The first classification of prosthetic devices has one solid component (excluding the head) that replaces a portion of the femur or humerus. This solid component can be viewed as having three sections, a stem section, a body section adjoining the stem section, and a neck section adjoining the body section. The stem section is an elongated section of the device that is inserted deeply into a channel reamed or machined into the bone to anchor the device in the femur or humerus. The stem section helps to prevent the device from rocking within the patient, and the stem section also spreads loads transmitted through the device over a larger area. The stem section may be straight, but many times the bone has a curvature or, as the bone is reamed or machined to receive the stem, the cutting device produces a curved channel into which the stem section must be inserted. Consequently, the stem section is often curved to fit either a curving bone or to fit wit a curving channel.

The second section of the solid-component implant is the body section. At least a portion of the body section fits within a cavity machined or broached into the end of the bone, where the bone widens. The body section is thus shaped to follow the widening shape of the bone, and the body section is also shaped to prevent the device from rotating within the bone in which the device is implanted. The body section also provides structural strength to the device as well as a large surface area for anchoring the device within the bone and for transmitting loads into the bone.

The third section of the solid-component implant is the neck section. The neck section adjoins the body section and provides an anchor point for the head at the correct angle and location to permit the head to properly engage the pelvis or the glenoid cavity.

The solid, one-component prosthesis described above enjoys wide-spread use. This prosthesis is used in roughly ninety percent of the hip implants currently performed in the U.S.

The second classification of prosthetic devices has two major components (excluding the head) that are fit together to form the device. One component of the two-component device embodies one of the three sections discussed above, and the other component embodies the other two sections. Thus, one component can be a combination of the stem and body sections, and its mating component is a neck component. Alternatively, one component can be a combination of the neck and body sections, and its mating component is a stem component. These devices are typified by those disclosed in U.S. Pats. No. 5,002,578, 5,002,581, 5,108,452, 5,135,529, 5,201,882, and 5,314,479. The devices disclosed in U.S. Pats. No. 5,080,685, 5,181,928, 5,286,260, and 5,370,706 are also considered two-component devices despite mention of three separate components in these patents, since the neck component described for those devices is no more than a screw used to hold the head to the body. In those devices, the angle and location of the head component are essentially determined by the screw-receiving bore within the body portion of the implant, making the body portion in effect a combined body/neck component.

Another classification of prosthetic devices has three major components (excluding the head). The device has a stem that inserts into the bone, a body that also inserts into the bone and into which the stem is mated, and a neck that mates to the body and to the head. One such device is disclosed in U.S. Pat. No. 5,002,578 (see especially FIG. 5).

Each of the three classifications of implants has problems or disadvantages associated with its design. The one-component device is usually forged from a blank or machined from a single block of metal. The blank used to forge the one-component device is costly, and if the one-component device is machined from a blank, much of the metal is lost during machining, and many complex and sequential machining steps must be performed to shape the finished device. The one-component device is, consequently, very expensive to manufacture. Also, because of the wide variety of shapes and sizes of femoral and humeral bones in the world's population, a distribution center or hospital must inventory a very large number of one-component devices having different dimensions in order to provide a prosthetic device that will fit a particular patient on whom surgery is being performed. However, to reduce inventory requirements, certain combinations of stem diameter and shape, body size and shape, and neck vertical and lateral offset are usually not supplied, which limits a surgeon's options in providing a prosthesis with a comfortable fit. If a hospital stocks sixty one-component devices, the surgeon has only sixty options from which to choose when fitting a patient with a prosthesis. Because of limited inventory, a surgeon can usually fit a patient with a prosthesis in which only one of the three sections (i.e. the head section, the neck section, is or the stem section) of the prosthesis fits well within the patient. The other two sections almost invariably are not ideally fit to the patient in whom the prosthesis is being implanted. Thus, with the one-component device, it is very difficult to have both a wide selection of fit and a reasonable inventory cost.

Further, precise installation of a single-component device within a patient can be very difficult, especially for a device in which the stem section is fluted to better anchor the device and prevent it from rotating. Once the flutes begin to encounter bone, the flutes cut their own channels to help anchor the implant. If the surgeon discovers that the implant does not fit as well as the surgeon wishes, the surgeon must dislodge the implant from the bone (causing further trauma) and either reposition the implant or remove the implant and substitute one having the appropriate dimensions before seating the implant once again. Despite these disadvantages, the one-component device remains the most widely-used implant today.

The two-component device also has a number of problems or disadvantages associated with its design. Like the one-component device, a component such as a combined neck-and-body component or a combined body-and-stem component typically requires many machining steps and is thus costly to make. Also, because of the wide variety of shapes and sizes of femoral and humeral bones in the population, a large number of these components must be inventoried by a hospital, or the hospital must select only certain sizes and compromise the fit of the device within the patient. An inventory of one hundred thirty pieces provides only approximately two hundred surgical options. At best, the surgeon can usually provide a good fit within a patient for two of the three (neck, body, and stem) sections.

Precise placement of the two-component device within a patient can also be very difficult where the body and neck sections or the stem and body sections are combined in one component, and especially where the stem is fluted and/or the channel in which the stem section is inserted is curved. A surgeon may need to remove and reinsert components similarly to the one-component device described above, causing additional trauma to the patient. Although the magnitude of these problems or disadvantages is somewhat reduced when compared to the problems associated with the one-component device, the magnitude of these problems remains significantly high for the two-component device.

The three-component device disclosed in U.S. Pat. No. 5,002,578 also has disadvantages associated with its design. The stem component and the body component must be joined to form a sub-assembly prior to implanting this sub-assembly within the patient. It is difficult to precisely align the stem component and body component outside of the patient's body so that a body component and a curved stem component have the correct relationship to one another to fit within the channel and the cavity formed in the bone, and it is also difficult to precisely position a sub-assembly during insertion into the bone to assure that the sub-assembly is accurately positioned within the bone as flutes on the stem cut into the bone and anchor the sub-assembly.

Thus, various devices discussed above have a number of disadvantages. A large number of parts must be stocked, which creates high inventory costs for hospitals. This also requires the surgeon to take precious time during an operation to select the correct component(s) from the large number in stock. The particular dimensions to which the device must be fit are not known until the patient has undergone surgery to remove part of the deteriorated bone and until the bone has been trimmed and reamed or broached to accept the stem and body of the device. Consequently, selection of components and their assembly is performed during surgery, and any time needed to select components, assemble, and adjust the device lengthens the time that the patient is undergoing surgery. Further, in an effort to control inventory costs, a hospital or company supplying the components may limit the number of components available, which forces the surgeon to compromise the fit and comfort of the prosthesis for many patients.

The parts are usually costly, since they require lengthy and complex machining procedures to manufacture them. The parts are also not easily adjusted when being installed into a patient. A slight misalignment of a component because of incorrect assembly causes the whole assembly to be very difficult to install. A slight misalignment is not known until the surgeon attempts to install the device in the patient. If the stem is attached to the body and is slightly misaligned so that it causes the body and neck not to fit in the patient properly, the assembled device must be removed from the patient, any bond between the stem and the body components must be broken, and the stem must be adjusted and rebonded to the body. The assembled device is reinserted into the patient, and if the stem is not yet properly aligned, the device must again be removed from the patient and the process repeated until the components in the device are properly aligned. It would clearly be advantageous if prostheses could be made having a wide variety of dimensions from few components that require little machining. It would further be clearly advantageous if prostheses could be made that are easily adjusted during surgery while installing these prostheses within patients.

It is an object of certain embodiments of this invention to provide a modular assembly having three major components that are easily and independently adjustable during their assembly into a patient. It is another object of certain embodiments of the invention to provide a three-component modular assembly in which the body and neck components individually can be rotated around the axis of the stem component to independently adjust their version angles during assembly of the prosthetic device. It is a further object of certain embodiments of the invention to provide a three-component modular assembly that is self-tightening. It is another object of certain embodiments of this invention to provide a modular assembly that can be quickly installed. It is another object of certain embodiments of this invention to provide a smaller set of components from which a surgeon will choose without reducing the number of combinations of fit of components, so that the surgeon can provide a patient with the combination of components that fit the patient's particular bone structures without requiring high inventory levels of components. It is another object of certain embodiments of this invention to provide an assembly of three components, each of which requires few machining steps to manufacture. Further objects and advantages of the invention are apparent from the discussion herein.

SUMMARY OF THE INVENTION

The invention provides a modular assembly of components that are used to replace a portion of a patient's femur or humerus, and the invention provides a method of assembling the components into a patient. The modular assembly of this invention comprises three major components, a neck component, a body component, and a stem component, wherein the neck component and the stem component engage with one another. In one preferred embodiment of the invention, the stem component and the neck component have shapes which allow the stem and neck components to engage one another, the body component and the neck component have shapes that allow these two components to mate together, and the three components are shaped so that the three components may be assembled together to form a prosthesis. Thus, the neck component of a preferred embodiment of an assembled modular assembly connects to both the body component and the stem component, providing a strong interlocking mechanism and eliminating the need to mate the stem component to the distal portion of the body component.

The invention also provides a unique method for assembling the modular assembly within a patient. An implant can be assembled by attaching a body component to a neck component and by attaching a stem component to the neck component, wherein the three components are shaped such that the three components may all be attached together to form one implant. This new method makes assembly of the components much easier, especially during surgery.

Among other factors, the invention is based on the technical finding that a three-component modular assembly having a neck component which engages a stem component as described herein can have many advantages over implants previously available. A surgeon can easily exchange e.g. a neck component or a body component for another component of different dimensions when inserting the components into the patient. This great flexibility during assembly of the prosthesis can both reduce the length of time required to operate on a patient and yet allow the surgeon to provide a patient with a comfortable prosthesis with a natural range of movement. The surgeon also has a high degree of flexibility in adjusting the position of the components during assembly, so that unnatural stresses are not introduced into the components when they are locked together to form the prosthesis and so that the patient is provided with a comfortable prosthesis that is not trying to twist or move into an unwanted position.

The invention is also based on the technical finding that a three-component modular assembly as described herein provides a large number of combinations of dimensions for the assembled device from very few components, reducing the inventory that a hospital must purchase. (In fact, over three thousand combinations of fit within a patient are possible from only fifty components, providing a surgeon with many options during surgery and providing a hospital with reasonable inventory costs.) A three-component modular assembly can reduce the amount of time required for the surgeon to select and assemble the components. Also, few machining steps are required to manufacture each of the components used in the three-component modular assembly of this invention when compared to one- or two-component devices, reducing the cost of components and the cost of an assembly. A prosthesis assembled from the three-component modular assembly of this invention can also be self-tightening in preferred embodiments of the invention. These features and advantages and others are apparent from the discussion herein, including the claims and the appended drawings which are incorporated by reference into the specification in their entirety.

BRIEF DESCRIPTION OF THE DRAWINGS

The Figures illustrate certain preferred embodiments of the invention, and, consequently, the claims are to be given their broadest interpretation that is consistent with the specification, the drawings, and the meaning of terms used herein to one of ordinary skill in the art.

DETAILED DESCRIPTION OF THE PREFERRED EMBODIMENT

The invention provides a modular assembly of components that can be assembled to form a prosthesis for replacing a portion of, e.g., the femur or the humerus. In one embodiment of the invention, the modular assembly comprises three components, a stem component, a body component, and a neck component, wherein the distal portion of the stem component has a shape which fits within the bone, the body component has a shape such that at least a portion of the body component fits within the bone, and the proximal portion of the stem component is shaped to engage with the neck component. The invention is better understood with reference to the accompanying Figures.

Figure 1:
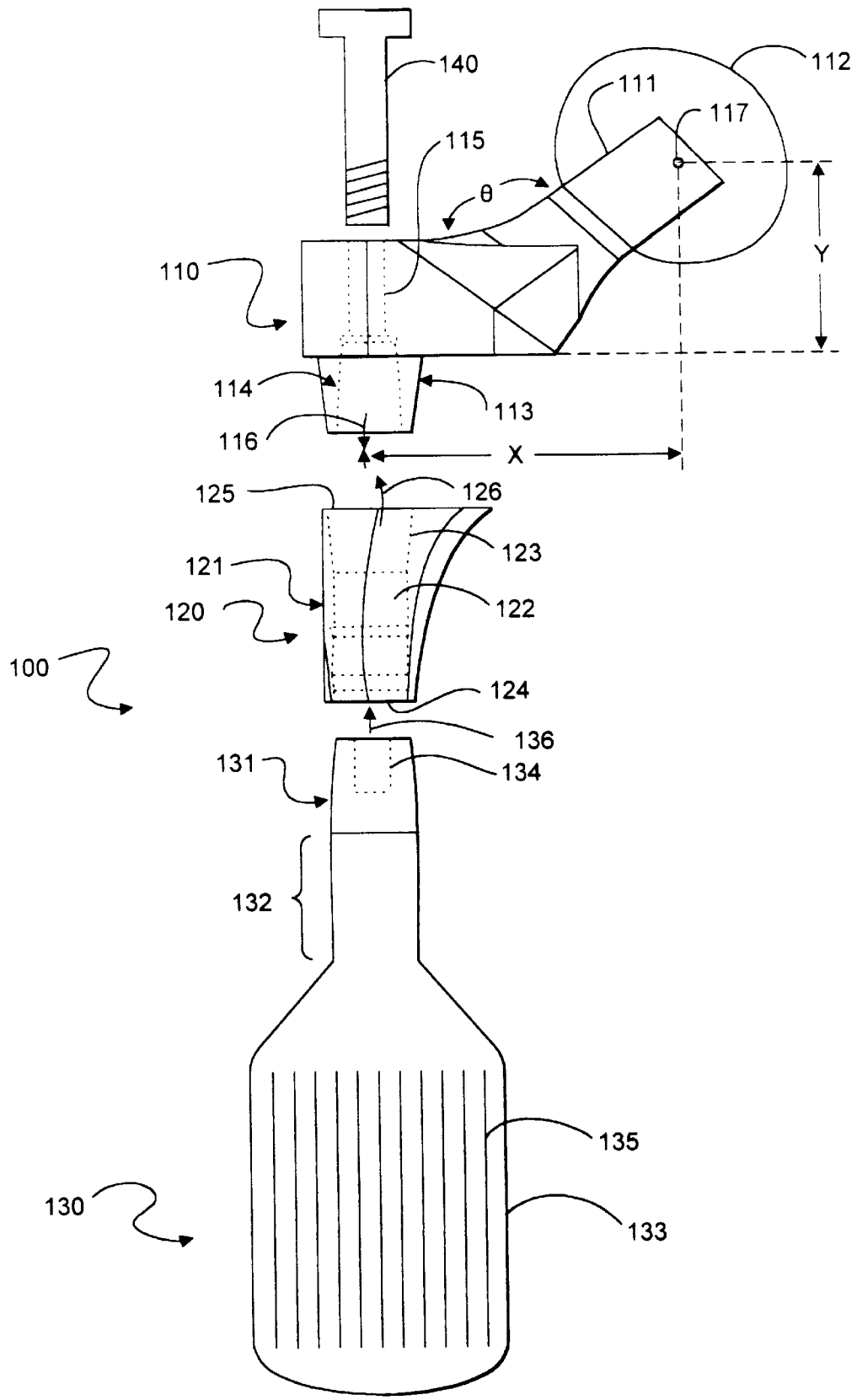
FIGS. 1 and 2 illustrate two embodiments of a modular assembly of this invention that are used to replace a portion of a femur and a portion of a humerus, respectively, wherein the neck component of the assembly has a male taper that inserts into a female taper in a body component, and a stem component has a male taper that inserts into a female taper in the neck component.
Figure 2:
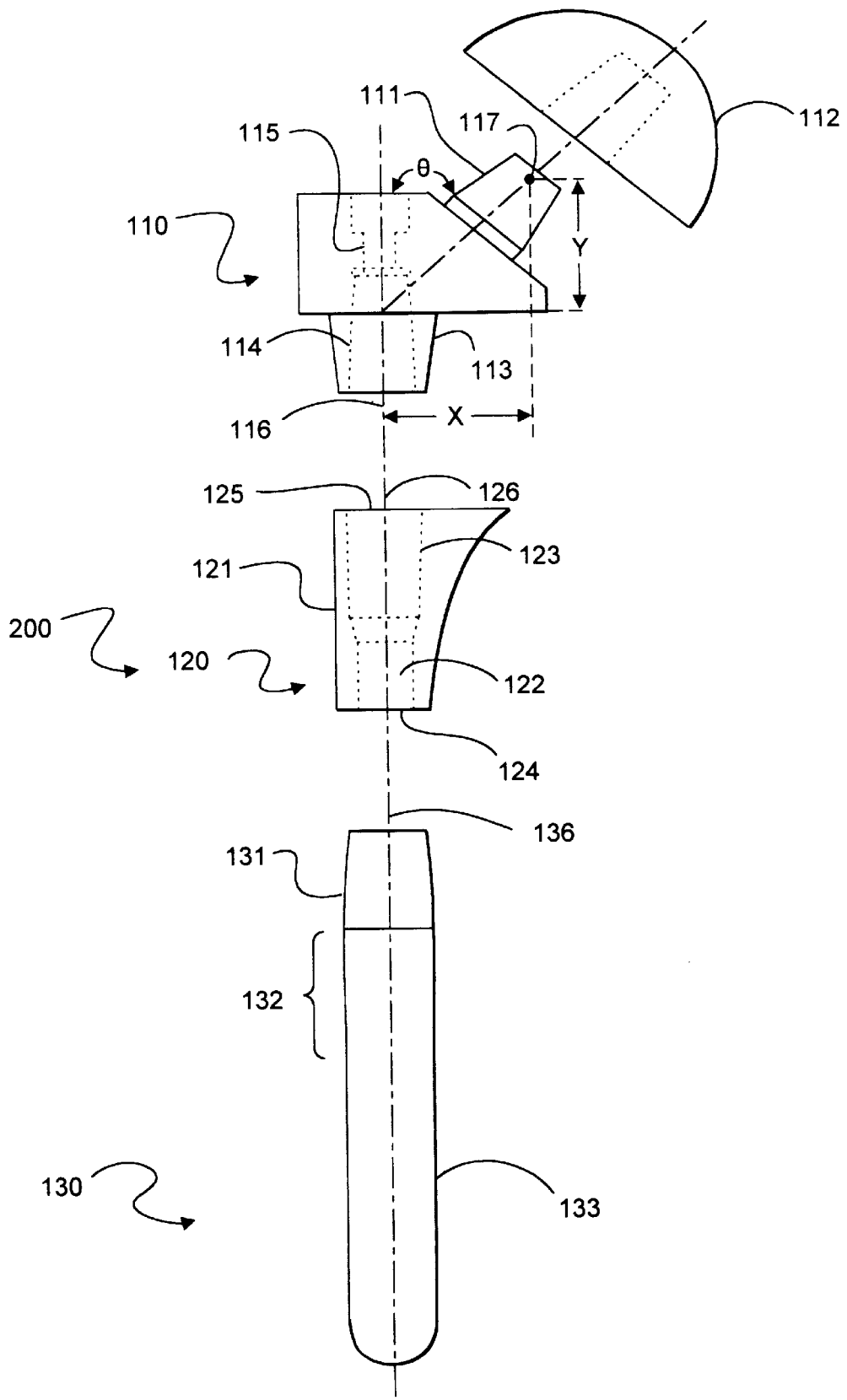

FIGS. 1 and 2 show two embodiments of an assembly of this invention. FIG. 1 illustrates an assembly 100 used to replace a portion of the femur, and FIG. 2 shows an assembly 200 used to replace a portion of the humerus. The assembly has a neck component 110, a body component 120, and a stem component 130. Neck component 110 has a proximal neck 111 that attaches to a head component 112 which fits into the patient's pelvic socket, or, if desired, the head component may be formed integrally as part of the neck component. Neck component 110 also has an outer male taper portion 113, an inner female taper portion 114, and a channel 115. The proximal neck portion forms an angle θ with the remainder of the neck component, as illustrated in FIGS. 1 and 2. The neck component has a lateral offset x, which is the shortest distance between a line that is perpendicular to the central axis of the taper portion 114 (i.e. the axis 116 of the neck component) and a line parallel to the axis line and intersecting the head center 117. Head center 117 is selected during design of the neck component and is the location of the center of mass $C_m$ for a standard head component. Neck component 110 also has a vertical offset y, measured by the shortest distance from a line drawn parallel to the position on the neck where the neck and body components join and to the head center 117 as described above. Lateral and vertical offsets x and y, respectively, are illustrated in FIGS. 1 and 2. For a hip implant, neck component 110 has the following typical dimensions: lateral offset typically is at least 20 mm and/or no more than 60 mm; vertical offset typically is at least 20 mm and/or no more than 50 mm; and θ is typically at least 127 and/or no more than 135 degrees. For a shoulder implant, neck component 110 has the following typical dimensions: lateral offset typically is at least 5 mm and/or no more a than 30 mm; vertical offset typically is at least 5 mm and/or no more than 30 mm; and θ is typically at least 127 and/or no more than 135 degrees.

Body component 120 has an outer shape 121, and at least a portion of the body component fits within part of the patient's femur or humerus. The outer shape and dimensions of body component 120 are determined to best fit a population from statistical information on the size and shape of patients' femur and humeral bones. Alternatively, a body component of customized shape and dimensions can be produced to fit an individual patient based on information from e.g. x-ray or magnetic resonance imaging or CT scans of the patient's bone. Body component 120 also has a stem-receiving cavity 122 within the body component and a female taper portion 123 within the stem-receiving cavity. The stem-receiving cavity is shaped to receive the stem component and to allow the stem component to pass through the distal end 124 and the proximal end 125 of the stem-receiving cavity sufficiently that the proximal taper portion 131 of the stem component is located within neck component 110 when the components are assembled together. The stem-receiving cavity can be shaped to contact the stem-receiving cavity contacting portion 132 of the stem component along its full length, or, the stem-receiving cavity can be tapered on its distal end so that the stem component does not contact the distal portion of the body component as the stem component flexes while the prosthesis is in use within a patient. Alternatively, the stem-receiving cavity can be shaped so that the stem component does not contact any portion of the body component forming the stem-receiving cavity as the stem component flexes while the prosthesis is in use within a patient. The axis 126 of the body component, a line drawn up through the center of the stem-receiving cavity 122, is substantially parallel to the axis of the neck component and the axis of the proximal portion of the stem component.

Stem component 130 has a taper portion 131 at its proximal end, a stem-receiving cavity contacting portion 132, and a distal stem portion 133. Stem component 130 is inserted into the patient's femur or humerus so that the axis 136 of the stem component coincides with the axis of the channel within the patient's bone and, in normal use, the stem component bears much of the load transmitted through the patient's hip and leg or shoulder and arm. The distal stem portion can be straight or curved, and the distal stem portion can have flutes 135, grooves, slots, or holes that help the stem component seat within the femur. The diameter and shape of the distal stem portion are selected to fit within the channel within the femur or humerus. The diameter of the distal stem portion for the humerus is typically at least 6 mm and/or no more than 16 mm, and the diameter of the stem for the femur is typically at least 8 mm and/or no more than 25 mm.

Portions of the stem component and/or the body component may be highly polished or have a porous coating, plasma spray, or hydroxylapatite coating or may be chemically etched or roughened to promote new bone growth and/or to bond with the other component. The stem component may also have very small ridges such as concentric circles or fine threads on male taper 131 of the stem component to promote better bonding of male taper 131 and female taper 114.

The neck, body, and stem components are designed to fit together and form an implant having the desired dimensions and structural strength to form a suitable replacement for portions of a patient's bone. The unique design of an assembly of this invention allows the use of a new procedure to assemble an implant and install the implant in a patient. Male taper 113 of the neck component fits within female taper 123 of the body component, and stem 130 can be inserted through the stem-receiving cavity within body component 120 to join male taper 131 of the stem component with female taper 114 of the neck component. A screw 140 or other cinching device can be inserted through channel 115 and into threaded portion 134 of stem component 130 to seat stem component 130 within neck component 110. The screw may optionally be left within the implant to further hold the components together, although the configuration of tapers on the neck, body, and stem components provides a self-tightening taper construction that can eliminate any need for a screw. When a patient in whom a prosthesis having a self-tightening taper construction as shown in FIG. 1 walks or runs, the patient's body weight forces the neck component down, while the stem component provides an equal force upward to support the weight above it. The taper portion of the neck component is driven into the female taper of the body component, which pinches the outer taper portion of the neck component and thus pinches the opposing and embedded taper of the stem component, helping to lock the two components together. Taper portion 113 of the neck component may optionally be split so that it spreads to further lock neck component 110 and body component 120 together, and the taper portion may also have a collet ring that interlocks with a channel within the female taper. This new method of assembling an implant, wherein the stem is inserted into the neck component and joins with the neck component, allows great flexibility in adjusting the implant during assembly, either in or out of the body.

For example, if a surgeon elects to construct an implant outside the patient and insert the finished implant into the patient, the surgeon can loosen the components from one another during implantation and rotate the components to correct for a misalignment that occurred either during assembly of the implant or during implantation of the device. The surgeon can also remove, e.g., the neck component or the body component and substitute one with different dimensions if the surgeon is not satisfied with its fit within the patient. The surgeon has over three thousand options to provide a well-fitted implant when the hospital stocks only fully components for a tree-component assembly of this invention. Previous implants do not provide such a wide range of choices to the surgeon for selecting, constructing, or adjusting the implant during surgery.

The modular assembly of this invention also allows use of a new procedure to assemble a prosthesis within the patient's body during surgery. After a patient has been prepared to receive the prosthesis, the surgeon selects a stem component of the appropriate diameter from a number of stem components available to the surgeon in the operating room. Each stem component has, for example, a distal stem component diameter and/or curvature that differs from the diameter and/or curvature of the other stem components in the operating room, so that the surgeon can select a stem that fits best within the patient's femur. Each stem component available to the surgeon in the operating room also has a proximal taper portion 131 of standardized size and cross-section and a stem-receiving cavity contacting portion 132 of standardized size and cross-section, so that all stem assemblies available to the surgeon in the operating room have identically-dimensioned proximal taper portions and stem-receiving cavity contacting portions.

The surgeon also has available in the operating room a number of body components. Each body component has a different outer shape 121 and size, but the opening-size and shape of the stem-receiving cavity 122 within the body component and the female taper 123 are standardized and thus identical among all of the body components available to the surgeon in the operating room. The surgeon selects a body component of the appropriate size and shape to fit within the femur and to provide the desired mechanical cooperation with the other components when assembled, providing the patient with a comfortable prosthesis having very good fit.

The surgeon also has available a number of neck components 110, each having different dimensions and/or different angles θ that the proximal neck portion forms with the remainder of the neck component. Each neck component has an identically-dimensioned male taper portion, female taper portion, and proximal neck portion, so that the neck component selected by the surgeon can fat with any body component and stem component. Thus, the surgeon needs only to be concerned with selecting a neck component of the appropriate dimensions and angle θ that provide the assembly with the correct mechanical cooperation of all components and provide the patient a natural range of movement. The surgeon also has available a number of head components 112 of different dimensions, which head components have a standardized and identically-dimensioned female taper 116 to match the taper of the proximal neck of the neck components available to the surgeon.

Once the surgeon has selected the stem component of the desired diameter, the surgeon selects a body component of the desired size and outer shape. The surgeon positions the stem component within the femur of the patient and optionally uses the stem component as a guide to machine or broach the femur to accept the body component, so that the body component fits more precisely with the particular stem component inserted into the femur. Once the surgeon has placed the stem component within the femur, the surgeon then places the body component over the stem component and into the femur, which results in the proximal taper portion of the stem component sticking out of the female taper portion of the body component. (Alternatively, the surgeon may place the body component into the femur and pass the stem component through the stem-receiving cavity 122 within the body component and into the femur, or the surgeon may position the body component on the neck component prior to placing the body component within the femur.) The surgeon can insert the proximal taper portion of the stem component, which is sticking out of the open end of the body component, into the female taper portion of the neck component and also insert the male taper portion of the neck component into the body component. Insertion of the proximal taper portion of the stem component into the female taper portion of the neck component can be performed essentially simultaneously with insertion of the male taper portion of the neck component into the female taper portion of the body component. Last, the surgeon selects a head component of the desired size and shape and positions the head component on the proximal neck of the neck component.

The surgeon has great flexibility to align or change components prior to mating each component with its corresponding mated component. The surgeon can assure proper positioning of the body component in the femur independently of the shape, size, or positioning of the stem component by rotating the body component. The surgeon can rotate the neck and/or body components about the axis of the stem component to adjust the version angle prior to mating the stem component to the neck component in order to provide the proper mechanical cooperation of components and to assure the proper geometry of the finished prosthesis within the patient. If the surgeon judges that the finished prosthesis does not have the desired geometry or dimensions, the surgeon can quickly adjust or remove one or more of the components and substitute another to adjust the geometry or dimensions of the prosthesis.

The surgeon completes assembly of the components by driving the neck component onto the stem component and also into the body component. The male taper portion of the neck component mates with the female taper portion of the body component, while the proximal taper portion of the stem component mates with the female taper portion of the neck component. The neck component can be driven onto or off of the stem component by using a tool that fits into channel 115 and threads into the top of the stem component, pulling or pushing the components together. Additionally, the stem component may by held to the neck component by a screw of standardized size and threading, which screw passes through channel 115 and threads into the top of the stem component.

The new procedure described above provides the surgeon with the flexibility to quickly assemble and adjust the prosthesis in the patient and disassemble the prosthesis to fit differently-sized components if the surgeon so desires. The new procedure does not depend on having the described standardized tapers and cavities, although standardized dimensions of such elements is helpful. The new procedure, which involves connecting the neck component to the proximal taper portion of the stem component, removes an element that previously complicated the surgeon's decisions on which components to select and assemble. In previous three-component prostheses wherein the stem component mated with the body component, it was necessary to select the length of each of the three components, the neck component, the body component and the stem component, such that the assembled pieces provided the correct length of prosthesis. Using the new method where the stem component engages with the neck component, it is only necessary to select a neck component and a stem component of the appropriate length to provide the desired length of finished prosthesis. This feature reduces the number of components needed to provide a variety of dimensions to the prosthesis when it is constructed. Also, since the length of the body component has no effect on the overall length of the assembled prosthesis, the body component can be designed to the correct size and shape to provide the best fit with the femur, and the design of the body component is not compromised by having to consider how the stem component is to connect with the body component.

Because of the flexibility of the thee-component modular design of this invention, fewer components need to be stocked at the hospital and made available in the operating room than for prior devices. For example, five neck components having different dimensions and ten body components having different dimensions provide fifty different combinations of dimensions from fifteen components of this invention. Because existing two-piece and three-piece designs have these dimensions embodied in only the body component, these existing two-piece and three-piece designs require up to fifty (50) different bodies to provide the same combination of dimensions supplied by fifteen (15) components of this invention. A surgeon thus chooses from fewer components during an operation and tests the fit of the components within the patient quickly before assembling the components, which reduces the length of time that the patient must spend in surgery.

The components of an assembly of this invention can be formed by e.g. casting metal into molds or by machining metal to form the components. Components used in this invention are much easier to machine than such complex components as combined head/neck components or combined head/stem components, and, consequently, an assembly of this invention can be produced more quickly and less expensively than many prior prostheses can be made.

Figure 3:
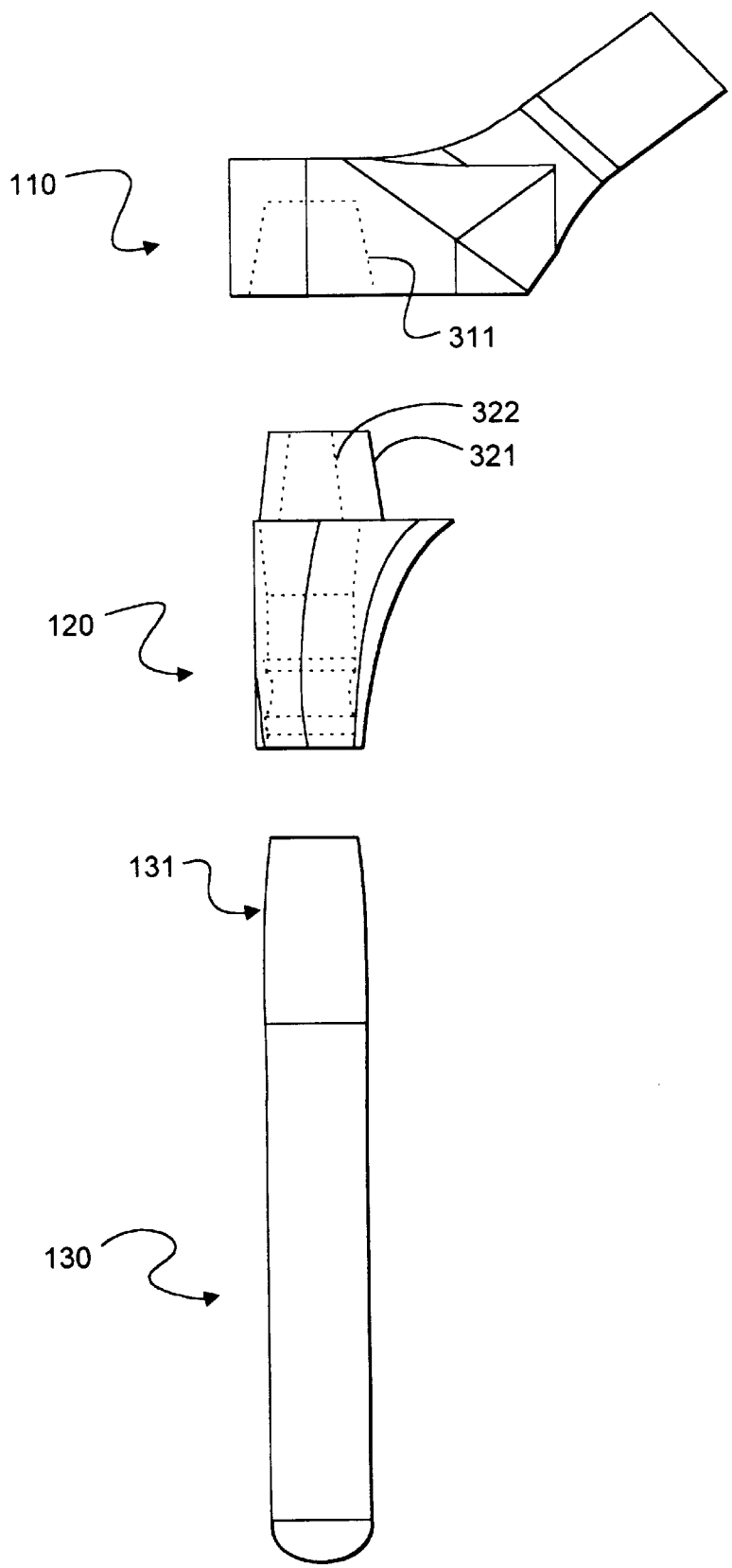
FIG. 3 illustrates a third embodiment of a modular assembly of this invention, wherein the body component has a male taper that inserts into a female taper in a neck component, and a stem component has a male taper that inserts into a female taper in the body component, which female taper is located within the neck component when the neck and body components are assembled together.

Another embodiment of the invention is illustrated in FIG. 3. Body component 120 has outer male taper 321 and inner female taper 322. Male taper 321 of body component 120 fits within female taper 311 of neck component 110, and proximal taper portion 131 of stem component 130 fits within female taper 322 which is located within neck component 120. Stem component 130 engages with neck component 110 through the taper portion of body component 120. The configuration of tapers shown in FIG. 3 provides a self-tightening taper construction. As a person with this implant walks or runs, the neck component pushes down onto the outer male taper of the body component, and the female taper of the neck component pinches the male taper of the body component and thus also pinches the embedded taper portion of the stem component. The neck component is better locked to the body component because of the downward force, and the stem component is also better locked to the body component by the pinching action of the taper section on the body component.

Also, since standard sizes and dimensions of the tapered portions of the components can be used, the lengths of the neck and stem components of this assembly determine the length of the assembly as described above, and the body component can be optimized to fit within the femur and provide the needed support and structural strength. Stem component 130 may also have two proximal taper portions, one of which extends through the taper portion 322 of body component 120 and into a corresponding female taper within the neck component, and one of which attaches to the taper portion 322 of the body component.

Figure 4:
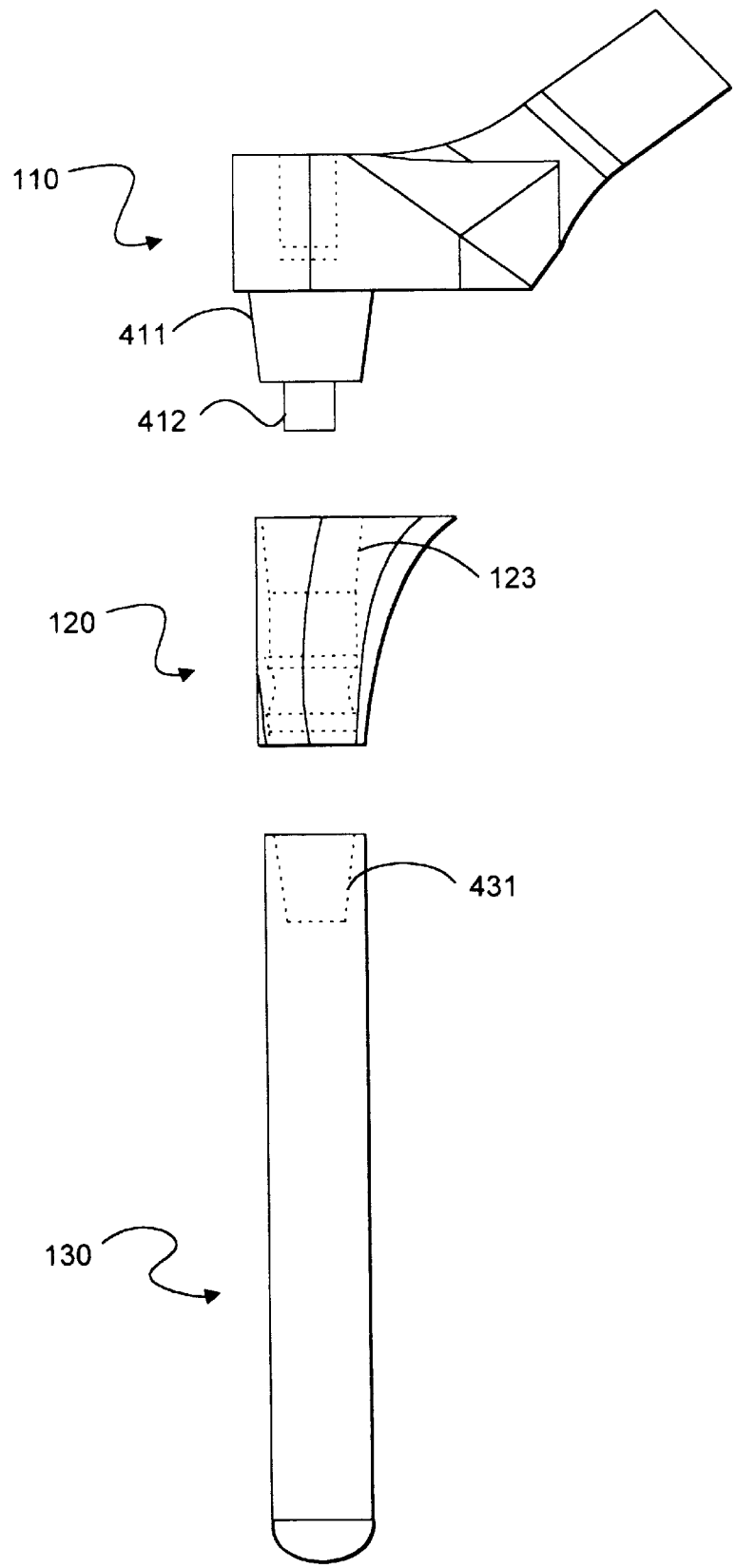
FIG. 4 illustrates a fourth embodiment of a modular assembly of this invention, wherein a neck component has two male tapers, one of which inserts into a female taper in a body component and one of which inserts into a female taper in a stem component.

FIG. 4 illustrates a fourth embodiment of the invention. The assembly of FIG. 4 has a neck component 110 with two male tapered portions 411 and 412 that fit within the body component 120. Male taper portion 411 mates with female taper portion 123 of body component 120, and male taper portion 412 mates with female taper portion 431 of stem component 130.

Figure 5:
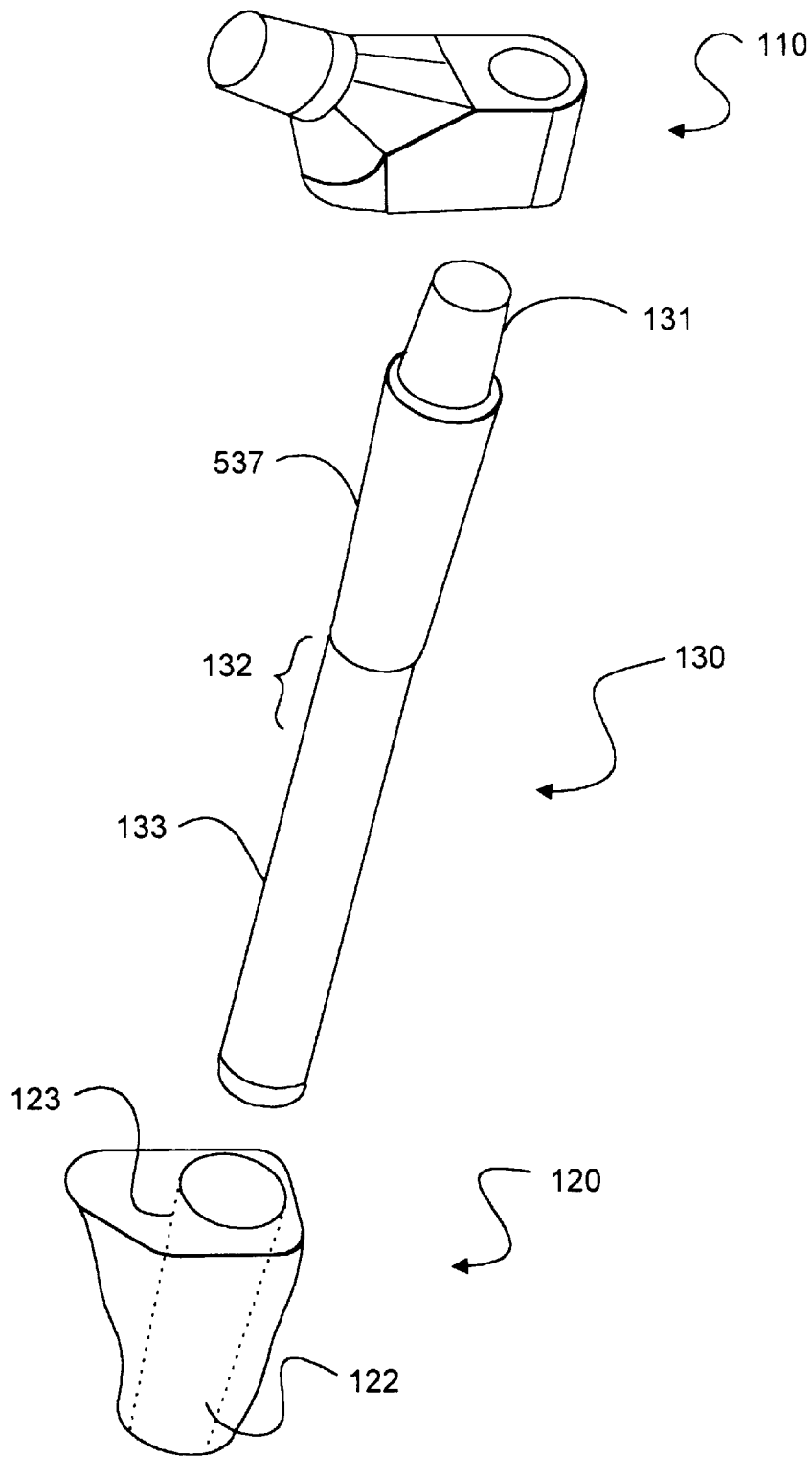
FIG. 5 illustrates a fifth embodiment of a modular assembly of this invention that is used to replace a portion of the femur, wherein the body component mates to the stem component through tapered portions of those components and the stem component mates to the neck component through tapered portions of those components.

It is not necessary for the body component to interlock with the neck component. The neck component can attach to the stem component by a taper, a stop on the diameter of the stem component (such as a ridge, bracket, or set-screw), a cement, or by other means that secure the body component to the stem component. For example, in the assembly illustrated in FIG. 5, male taper 537 on stem component 130 mates with female taper 123 of body component 120, while male taper 131 of stem component 130 mates with a corresponding female taper (not shown for sake of clarity of the drawings) in neck component, 110.

The embodiments above illustrate that the neck component of an assembly of this invention can be rotated about an axis that is parallel to the axis of the body component or the stem component. Thus, the position of the neck component does not depend on the position of the body component or the stem component, and the neck component can be adjusted independently of the body component and the stem component. Likewise, the body component can be rotated about the axis of the stem component, and its angle can be adjusted independently of the stem position or the neck position. As discussed previously, these features provide the surgeon with the ability to easily and quickly adjust the fit of the prosthesis within the patient without having to remove and reinsert the prosthesis during surgery.

Descriptions of specific designs and dimensions are provided only as examples. It is to be understood that various modifications to the preferred embodiments will be readily apparent to those skilled in the art, and that one skilled in the art can easily adapt the sizes and shapes of the components of this invention for replacement of a portion of the humerus. Thus, while preferred embodiments of the invention have been disclosed, it will be readily apparent to those skilled in the art that the invention is not limited to the disclosed embodiments but, on the contrary, is intended to cover numerous other modifications and broad equivalent arrangements that are included within the spirit and scope of the following claims.

What is claimed is:

1. A method of assembling a modular assembly that is used in the replacement of a portion of a bone, wherein the method comprises the steps of:

a. providing said modular assembly, wherein said modular assembly comprises a neck component having a first tapered portion, a body component having a second tapered portion, and a stem component having a third tapered portion, said body component is shaped to receive said stem component within said body component, and said components are shaped to replace a portion of the bone;
   b. attaching said body component to said neck component or said stem component;
   c. inserting said stem component into said neck component so that the third tapered portion of said stem component is located within the first tapered portion of said neck component; and
   d. joining the stem component to the neck component.

2. The method of claim 1, wherein inserting said stem component into said neck component further comprises inserting said stem component into the distal portion of a stem-receiving cavity within said body component and passing said stem component through said stem-receiving cavity prior to inserting the third tapered portion of the stem component into the first tapered portion of the neck component.

3. The method of claim 1, wherein inserting said stem component into said neck component further comprises inserting said stem component into the proximal portion of a stem-receiving cavity within said body component and passing said stem component at least partially through said stem-receiving cavity prior to inserting the third tapered portion of the stem component into the first tapered portion of the neck component.

4. The method of claim 2, wherein the body component is at least partially attached to the neck component prior to passing the stem component through the stem-receiving cavity of the body component.

5. A method of assembling a modular assembly with a self-tightening construction that is used in the replacement of a portion of a bone, wherein the method comprises the steps of:

1. providing said modular assembly, wherein said modular assembly comprises a neck component having a first tapered portion, a body component having a second tapered portion, and a stem component having a third tapered portion, said body component is shaped to receive said stem component within said body component, and said components are shaped to replace a portion of the bone;
   2. attaching said body component to said neck component or said stem component;
   3. inserting said stem component into said neck component so that the third tapered portion of said stem component is located within the first tapered portion of said neck component;
   4. joining the stem component to the neck component; and
   5. tightening said modular assembly within the patient's body.

6. The method of claim 5, wherein tightening said modular assembly further comprises tightening when the patient walks or runs.

7. The method of claim 5, wherein tightening the modular assembly further comprises tightening via the application of a force from a patient's body weight.

8. The method of claim 5, wherein tightening the modular assembly further comprises driving the first tapered portion into the second tapered portion.

9. The method of claim 5, wherein inserting said stem component into said neck component further comprises inserting said stem component into the distal portion of a stem-receiving cavity within said body component and passing said stem component through said stem-receiving cavity prior to inserting the third tapered portion of the stem component into the first tapered portion of the neck component.

10. The method of claim 5, wherein inserting said stem component into said neck component further comprises inserting said stem component into the proximal portion of a stem-receiving cavity within said body component and passing said stem component at least partially through said stem-receiving cavity prior to inserting the third tapered portion of the stem component into the first tapered portion of the neck component.

11. The method of claim 9, wherein the body component is at least partially attached to the neck component prior to passing the stem component through the stem-receiving cavity of the body component.

12. A method of assembling a modular assembly that is used in the replacement of a bone structure, wherein the method comprises the steps of:
 a. providing said modular assembly, wherein said modular assembly comprises a neck component having a first tapered portion, a body component having a second tapered portion, and a stem component having a third tapered portion, said body component is shaped to receive said stem component within said body component, and said components are shaped to replace a portion of the bone structure;
 b. attaching said body component to said neck component or said stem component;
 c. inserting said stem component into said neck component so that the third tapered portion of said stem component is located within the first tapered portion of said neck component; and
 d. joining the stem component to the neck component.

13. The method of claim 12, wherein inserting said stem component into said neck component further comprises inserting said stem component into the distal portion of a stem-receiving cavity within said body component and passing said stem component through said stem-receiving cavity prior to inserting the third tapered portion of the stem component into the first tapered portion of the neck component.

14. The method of claim 12, wherein inserting said stem component into said neck component further comprises inserting said stem component into the proximal portion of a stem-receiving cavity within said body component and passing said stem component at least partially through said stem-receiving cavity prior to inserting the third tapered portion of the stem component into the first tapered portion of the neck component.

15. The method of claim 13, wherein the body component is at least partially attached to the neck component prior to passing the stem component through the stem-receiving cavity of the body component.

16. A method of assembling a modular assembly that is used in the replacement of a portion of a femur, wherein the method comprises the steps of:
 a. providing said modular assembly, wherein said modular assembly comprises a neck component having a first tapered portion, a body component having a second tapered portion, and a stem component having a third tapered portion, said body component is shaped to receive said stem component within said body component, and said components are shaped to replace a portion of the femur;
 b. attaching said body component to said neck component or said stem component;
 c. inserting said stem component into said neck component so that the third tapered portion of said stem component is located within the first tapered portion of said neck component; and
 d. joining the stem component to the neck component.

17. The method of claim 16, wherein inserting said stem component into said neck component further comprises inserting said stem component into the distal portion of a stem-receiving cavity within said body component and passing said stem component through said stem-receiving cavity prior to inserting the third tapered portion of the stem component into the first tapered portion of the neck component.

18. The method of claim 16, wherein inserting said stem component into said neck component further comprises inserting said stem component into the proximal portion of a stem-receiving cavity within said body component and passing said stem component at least partially through said stem-receiving cavity prior to inserting the third tapered portion of the stem component into the first tapered portion of the neck component.

19. The method of claim 17, wherein the body component is at least partially attached to the neck component prior to passing the stem component through the stem-receiving cavity of the body component.

20. The method of claim 16, further comprising inserting of the stem component into the femur, before attaching said body component to said neck component or said stem component.

21. The method of claim 16, further comprising inserting of the modular assembly into the patient, after joining the stem component to the neck component.

22. A method of assembling a modular assembly that is used in the replacement of a portion of a humerus, wherein the method comprises the steps of:
 a. providing said modular assembly, wherein said modular assembly comprises a neck component having a first tapered portion, a body component having a second tapered portion, and a stem component having a third tapered portion, said body component is shaped to receive said stem component within said body component, and said components are shaped to replace a portion of the humerus;
 b. attaching said body component to said neck component or said stem component;
 c. inserting said stem component into said neck component so that the third tapered portion of said stem component is located within the first tapered portion of said neck component; and
 d. joining the stem component to the neck component.

23. The method of claim 22, wherein inserting said stem component into said neck component further comprises inserting said stem component into the distal portion of a stem-receiving cavity within said body component and passing said stem component through said stem-receiving cavity prior to inserting the third tapered portion of the stem component into the first tapered portion of the neck component.

24. The method of claim 22, wherein inserting said stem component into said neck component further comprises inserting said stem component into the proximal portion of a stem-receiving cavity within said body component and passing said stem component at least partially through said stem-receiving cavity prior to inserting the third tapered portion of the stem component into the first tapered portion of the neck component.

25. The method of claim 23, wherein the body component is at least partially attached to the neck component prior to passing the stem component through the stem-receiving cavity of the body component.

26. The method of claim 22, further comprising inserting of the stem component into the humerus, before attaching said body component to said neck component or said stem component.

27. The method of claim 22, further comprising inserting of the modular assembly into the patient, after joining the stem component to the neck component.

* * * * *

UNITED STATES PATENT AND TRADEMARK OFFICE
CERTIFICATE OF CORRECTION

PATENT NO. : 5,902,340
DATED : May 11, 1999
INVENTOR(S) : Patrick M. White, et al.

It is certified that error appears in the above-identified patent and that said Letters Patent is hereby corrected as shown below:

Column 1, on or around printer line number 35, "fit wit" should be --fit with--.

Column 2, on or around printer line number 43, "section, is or the stem" should be --section, or the stem--.:

Column 6, on or around printer line number 49, "more a than" should be --more than--.

Signed and Sealed this

Thirteenth Day of June, 2000

Attest:

Q. TODD DICKINSON

Attesting Officer          Director of Patents and Trademarks